United States Patent [19]
Everhart, III

[11] Patent Number: 5,956,689
[45] Date of Patent: Sep. 21, 1999

[54] SYSTEMS, METHODS AND COMPUTER PROGRAM PRODUCTS FOR USING EVENT SPECIFICITY TO IDENTIFY PATIENTS HAVING A SPECIFIED DISEASE

[75] Inventor: Kenneth A. Everhart, III, Jamestown, N.C.

[73] Assignee: Accordant Health Services, Inc., Greenboro, N.C.

[21] Appl. No.: 08/904,970

[22] Filed: Jul. 31, 1997

[51] Int. Cl.[6] .......................... G06F 159/00; G06F 17/60
[52] U.S. Cl. .................................... 705/3; 705/2
[58] Field of Search ................. 705/2, 3, 1; 600/300, 600/301, 483

[56] References Cited

U.S. PATENT DOCUMENTS

| | | | |
|---|---|---|---|
| 5,018,067 | 5/1991 | Mohlenbrock et al. | 600/300 |
| 5,199,439 | 4/1993 | Zimmerman et al. | 600/483 |
| 5,253,361 | 10/1993 | Thurman et al. | 364/225 |
| 5,255,187 | 10/1993 | Sorensen | 600/300 |
| 5,262,943 | 11/1993 | Thibado et al. | 600/300 |
| 5,265,010 | 11/1993 | Evans-Paganelli et al. | 600/301 |
| 5,319,543 | 6/1994 | Wilhelm | 705/3 |
| 5,327,341 | 7/1994 | Whalen et al. | 705/3 |
| 5,404,292 | 4/1995 | Hendrickson | 600/301 |
| 5,410,471 | 4/1995 | Alyfuku et al. | 600/300 |
| 5,508,912 | 4/1996 | Schneiderman | 705/3 |
| 5,517,405 | 5/1996 | McAndrew et al. | 705/2 |
| 5,544,044 | 8/1996 | Leatherman | 705/3 |
| 5,557,514 | 9/1996 | Seare et al. | 705/2 |
| 5,594,637 | 1/1997 | Eisenberg et al. | 705/2 |
| 5,642,936 | 7/1997 | Evans | 600/300 |
| 5,687,716 | 11/1997 | Kaufmann et al. | 600/300 |
| 5,706,441 | 1/1998 | Lockwood | 705/3 |
| 5,724,379 | 3/1998 | Perkins et al. | 705/2 |
| 5,746,204 | 5/1998 | Schauss | 600/300 |
| 5,769,074 | 6/1998 | Barnhill et al. | 600/300 |
| 5,778,345 | 7/1998 | McCartney | 705/2 |
| 5,794,208 | 8/1998 | Goltra | 705/3 |
| 5,800,347 | 9/1998 | Skates et al. | 600/300 |
| 5,832,448 | 11/1998 | Brown | 705/2 |

OTHER PUBLICATIONS

Huff et al, "Using Hospital Discharge Data for Disease Surveillance", U.S. Department of Health and Human Resources Public Health Reports, vol. 111, No. 1, Jan. 1996, p. 78.

Huff et al., "Using Hospital Discharge Data for Disease Surveillance", U.S. Department of Health and Human Services Public Health Reports, vol. 111, No. 1, Jan. 1996. p. 78.

*Primary Examiner*—Emanuel Todd Voeltz
*Assistant Examiner*—John W. Hayes
*Attorney, Agent, or Firm*—Myers Bigel Sibley & Sajovec, P.A.

[57] ABSTRACT

Systems, methods and computer program products are provided for identifying members of a population having a specified disease state. First and second sets of medical events associated with a disease state are identified. Each member of first and second population subsets have at least one medical event from the first and second sets of medical events, respectively. A third population subset is created comprising members of the first population subset who are not members of the second population subset. A specificity rating, indicating how often a respective medical event occurred within the second population subset relative to the third population subset, is assigned to each medical event associated with members of the second population subset. A third set of medical events associated with members of the second population subset is identified, each of the identified medical events having a specificity rating above the selected threshold. A fourth population subset is created from the third population subset, each member of the fourth population subset having associated therewith at least one medical event from the third set of medical events. The second and fourth population subsets are combined, thereby identifying members of the population having a specified disease state.

28 Claims, 9 Drawing Sheets

SYSTEMS, METHODS AND COMPUTER PROGRAM PRODUCTS FOR USING EVENT SPECIFICITY TO IDENTIFY PATIENTS HAVING A SPECIFIED DISEASE

FIELD OF THE INVENTION

The present invention relates generally to data processing systems, methods, and computer products, and more particularly to medical diagnostic data processing systems, methods, and computer products.

BACKGROUND OF THE INVENTION

A rare chronic disease has a relatively low incidence rate among the general population, yet it afflicts a patient having it for the patient's lifetime. Examples of rare chronic diseases include Multiple Sclerosis, Myasthenia Gravis, CIDP, Myositis, Parkinson's Disease, Hemophilia, Sickle Cell Anemia, Cystic Fibrosis, Lupus, among others. The treatment of rare chronic diseases can be very costly. For example, average medical claims for patients having Hemophilia and Myasthenia Gravis often presently exceed $40,000 per year. For patients experiencing severe complications related to these diseases, annual costs may presently exceed $100,000–$300,000.

Typically, patients with rare chronic diseases receive fragmented and costly health care. Often, they see doctors not trained to handle their specific diseases and/or they delay care until their health is deteriorated to the point of needing expensive hospitalization. As a result, patient records are widely dispersed and providers rarely have a complete understanding of a patient's condition.

Health care costs for patients with rare chronic diseases may be reduced by carefully assessing a patient's condition and by developing a comprehensive individualized care plan. Early identification of patients having a rare chronic disease is important to the implementation of an individualized, cost effective care plan. Unfortunately, early identification of persons having rare chronic diseases from a large population of patients is often difficult.

Early detection of rare chronic diseases is often hampered because of the lack of experience health care providers have with respect to a particular disease. For example, an estimated 25,000 Americans are stricken annually with Myasthenia Gravis. Unfortunately, most health care providers seldom see patients with Myasthenia Gravis. On average, a neurologist may see only one or two such cases per year. Consequently, many patients having rare chronic diseases go undiagnosed, often for extended periods of time. Furthermore, this lack of experience with rare chronic disease often hinders effective and efficient treatment once a disease is diagnosed.

Also hampering early detection of rare chronic diseases are problems associated with medical and insurance records. For example, a patient having a rare chronic disease may be diagnosed properly, but due to a data entry error, the medical records do not accurately reflect the diagnosis. It is estimated that data entry errors exist in about ten percent of all claims histories.

SUMMARY OF THE INVENTION

It is therefore an object of the present invention to provide data processing systems, methods, and computer products for facilitating the identification of patients having rare chronic diseases.

It is another object of the present invention to provide data processing systems, methods, and computer products for facilitating early identification of patients having rare chronic diseases utilizing information from the medical claims histories of these patients.

These and other objects are accomplished, according to the present invention, by systems, methods and computer program products for identifying, with high reliability, members of a population having rare chronic diseases. Typically, insurance companies and health care providers maintain databases containing medical histories and insurance claim information of patients. Within these databases, medical codes are assigned to most items, including symptoms, past treatments, diagnoses, and the like. The present invention identifies patients having rare chronic diseases by applying various templates and statistical analyses to the information within these databases. A template for each rare chronic disease may include a set of medical codes associated with the particular disease, as well as combinations of medical codes that are associated with each disease. These code combinations may be based on various things such as: race, sex, age, time, as well as on boolean relationships, such as medical code A and C, but not B. Various manual reviews by experts or expert systems may also be included.

Operations performed in accordance with the invention include identifying a first set of medical events associated with a rare chronic disease. A first population subset from the population is created, wherein each member of the first subset has associated therewith at least one medical event from the identified first set of medical events. A second set of medical events associated with the rare chronic disease is then identified. A second population subset is created from the first population subset, wherein each member of the second population subset has associated therewith at least one medical event from the identified second set of medical events. A third population subset is then created which includes members of the first population subset who are not members of the second population subset. A frequency of occurrence is then determined for each medical event associated with members of the second population subset. A frequency of occurrence is also determined for each medical event associated with members of the third population subset.

Next, a specificity rating is assigned to each medical event associated with members of the second population subset. Each specificity rating identifies how often a respective medical event occurred within the second population subset relative to the third population subset. A third set of medical events associated with members of the second population subset is then identified. Each of the medical events within the third set has a specificity rating above a selected threshold. A fourth population subset is then created from the third population subset. Each member of the fourth population subset has associated therewith at least one medical event from the third set of medical events. The second and fourth population subsets are then combined to identify members of the population having a rare chronic disease.

The present invention is advantageous because existing medical and insurance records can be used to accurately identify patients having a specified disease state, such as a rare chronic disease. As a result, quality health care, that is also cost effective, can be provided to these patients.

DETAILED DESCRIPTION OF PREFERRED EMBODIMENTS

Figure 1:
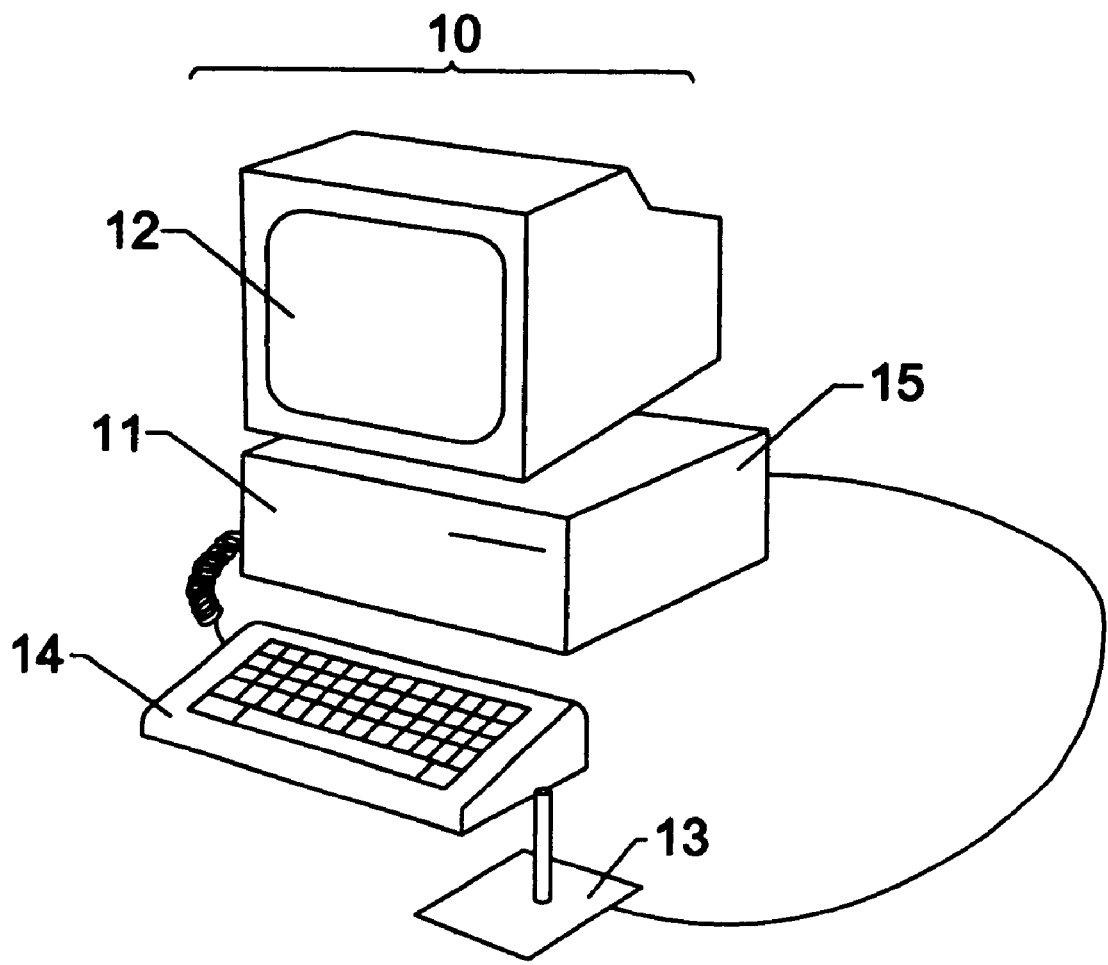
FIG. 1 schematically illustrates a data processing system for carrying out operations according to the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As will be appreciated by one of skill in the art, the present invention may be embodied as a method, data processing system, or computer program product. Accordingly, the present invention may take the form of an entirely hardware embodiment, an entirely software embodiment or an embodiment combining software and hardware aspects. Furthermore, the present invention may take the form of a computer program product on a computer-readable storage medium having computer-readable program code means embodied in the medium. Any suitable computer readable medium may be utilized including hard disks, CD-ROMs, optical storage devices, or magnetic storage devices.

The present invention is described below with reference to flowchart illustrations of methods, apparatus (systems) and computer program products according to the invention. It will be understood that each block of the flowchart illustrations, and combinations of blocks in the flowchart illustrations, can be implemented by computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Accordingly, blocks of the flowchart illustrations support combinations of means for performing the specified functions, combinations of steps for performing the specified functions and program instruction means for performing the specified functions. It will also be understood that each block of the flowchart illustrations, and combinations of blocks in the flowchart illustrations, can be implemented by special purpose hardware-based computer systems which perform the specified functions or steps, or combinations of special purpose hardware and computer instructions.

Referring now to FIG. 1, a typical data processing system 10 within which the present invention can be implemented is schematically illustrated. The system 10 preferably includes a central processing unit 11, a display 12, a pointing device 13, a keyboard 14, and access to persistent data storage 15. The keyboard 14, having a plurality of keys thereon, is in communication with the central processing unit 11. A pointing device 13, such as a mouse, may also be connected to the central processing unit 11. The central processing unit 11 contains one or more microprocessors (not shown) or other computational devices and random access memory (not shown) or its functional equivalent, including but not limited to, RAM, FLASHRAM, and VRAM for storing programs therein for processing by the microprocessor(s) or other computational devices.

Preferably, the central processing unit 11 is an Intel® 80386 processor (or equivalent) with at least eight megabytes (8 MB) of RAM, and at least five megabytes (5 MB) of persistent computer storage 15 for caching. Even more preferable is an Intel® 80486 or Pentium® processor (or equivalent). However, it is to be understood that various processors may be utilized to carry out the present invention without being limited to those enumerated herein. The system 10, if an IBM®, or IBM-compatible personal computer, preferably utilizes either a DOS, Windows® 3.1, Windows 95®, Windows NT®, Unix®, or OS/2® operating system. However, it is to be understood that the present invention may be implemented using other processors and via other computing devices, including, but not limited to, mainframe computing systems and mini-computers.

Table 1 below contains a listing of various rare chronic diseases along with a respective primary International Classification of Diseases (ICD) code.

TABLE 1

| CATEGORY | RARE/CHRONIC DISEASE | PRIMARY ICD CODE |
| --- | --- | --- |
| Neurology | Parkinson's Disease | 332.0 |
| | Multiple Sclerosis | 340.0 |
| | Acute Infective Polyneuritis (Guillian-Barre syndrome and CIDP) | 357.0 |
| | Myasthenia Gravis | 358.0 |
| | Myasthenic syndromes in diseases classified elsewhere | 358.1 |
| | Other specified myoneural disorders | 358.8 |
| | Myoneural disorders -unspecified | 358.9 |
| | Dermatomyositis | 710.3 |
| | Polymyositis | 710.4 |
| | Inclusion body myositis | 729.1 |
| Rheumatology | Systemic Lupus Erythematosus | 710.0 |
| | Systemic Sclerosis | 710.1 |
| | Rheumatoid Arthritis | 714.0 |
| Hematology | Gaucher's Disease | 272.7 |
| | Beta Thalassemia | 282.4 |
| | Sickle Cell Anemia | 282.6 |
| | Hemophilia | 286.0 |
| Pulmonology | Cystic Fibrosis | 277.0 |
| | Genetic Emphysema | 277.6 |

Each rare chronic disease may have supplementary ICD codes, procedure codes, and symptom codes associated therewith, as illustrated below in Table 2.

TABLE 2

MULTIPLE SCLEROSIS

| Primary ICD9 Code | Disease | | |
|---|---|---|---|
| 340 | Multiple Sclerosis | | |
| 341.9 | Demyellnating disease of central nervous system | | |
| Procedure Code | | 00405-4643* | Methotrexate |
| 70551 | Brain MRI | 00555-0572* | Methotrexate |
| 70552 | Bran MRI | 0781-1076* | Methotrexate |
| 70553 | Brain MRI | 00182-1539* | Methotrexate |
| 62270 | Lumbar Puncture | 00839-7905* | Methotrexate |
| | | 00205-532* | Methotrexate |
| ICD9 Symptoms Codes | | 00205-5337* | Methotrexate |
| 368.2 | Dipiopia | 53905-003* | Methotrexate |
| 379.5 | Nystagmua | 00205-4654* | Methotrexate |
| 728.9 | Muscular weakness | 00205-4556* | Methotrexate |
| NDC Code | Primary Medication | | |
| 50419-0521* | Betaseron | 00028-0023* | Lioresal /Baclofen |
| 59627-001-03 | avonex | 00028-0033* | Lioresal /Baclofen |
| | | 00405-411* | Baclofen |
| NDC Code | Secondary Medication | 57783-6980* | Baclofen |
| 00009-0113* | Solu-Medrol | 00332-223* | Baclofen |
| 00009-0190* | Solu-Medrol | 00781-164* | Baclofen |

TABLE 3

CYSTIC FIBROSIS

| Primary ICD Code | Disease | | |
|---|---|---|---|
| 277.0 | Cystic fibrosis | | |
| 277.00 | CF w/o mention of meconium lleus | | |
| 277.01 | CF with meconium lleus | | |
| ICD9 Procedure | | | |
| 33.5 | Lung Transplant | | |
| CPT Code | Procedure | | |
| 82438 | Sweat Chloride | | |
| 59360 | Sweat Chloride collection/lontophoreals | | |
| 94668 | Chest Wall manipulation | | |
| Supplemental ICD9 Codes | Symptoms | NDC Code | Primary Medication |
| 518.81 | Respiratory failure | 502420100 | Pulmozyma |
| 581.82 | Acute respitory distress/insufficiency | | |
| 786 | Respiratory disorder | 450095 | Pancrease |
| | | 5500530400 | Pancote |
| NDC Code | Secondary Medication | 550530400 | Pancote |
| | | 315025 | Entolase |
| 00074-3577* | Tobaramycin | 6035021 | Panase |
| 00074-3578* | Tobarmycin | 597430025 | Pancrellpase |
| 00074-3489 | Tobaramycin | 7812219 | Pancrellpase |

Medical records and insurance claims histories often include patient information such as: identification numbers, age, gender, diagnosis date of service, diagnosis code or name, procedure date of service, procedure code or name, drug date of service, drug code or name, health care provider type, and health care service provided. The present invention facilitates identifying patients having a specified disease state, such as a rare chronic disease, based on statistical information gleaned from these records. The present invention is not limited to the identification of rare chronic diseases. The present invention may be utilized to identify members of a population having various disease states as well as other characteristics and traits utilizing information within medical records, legal records, historical records, insurance records, and the like.

Figure 2:
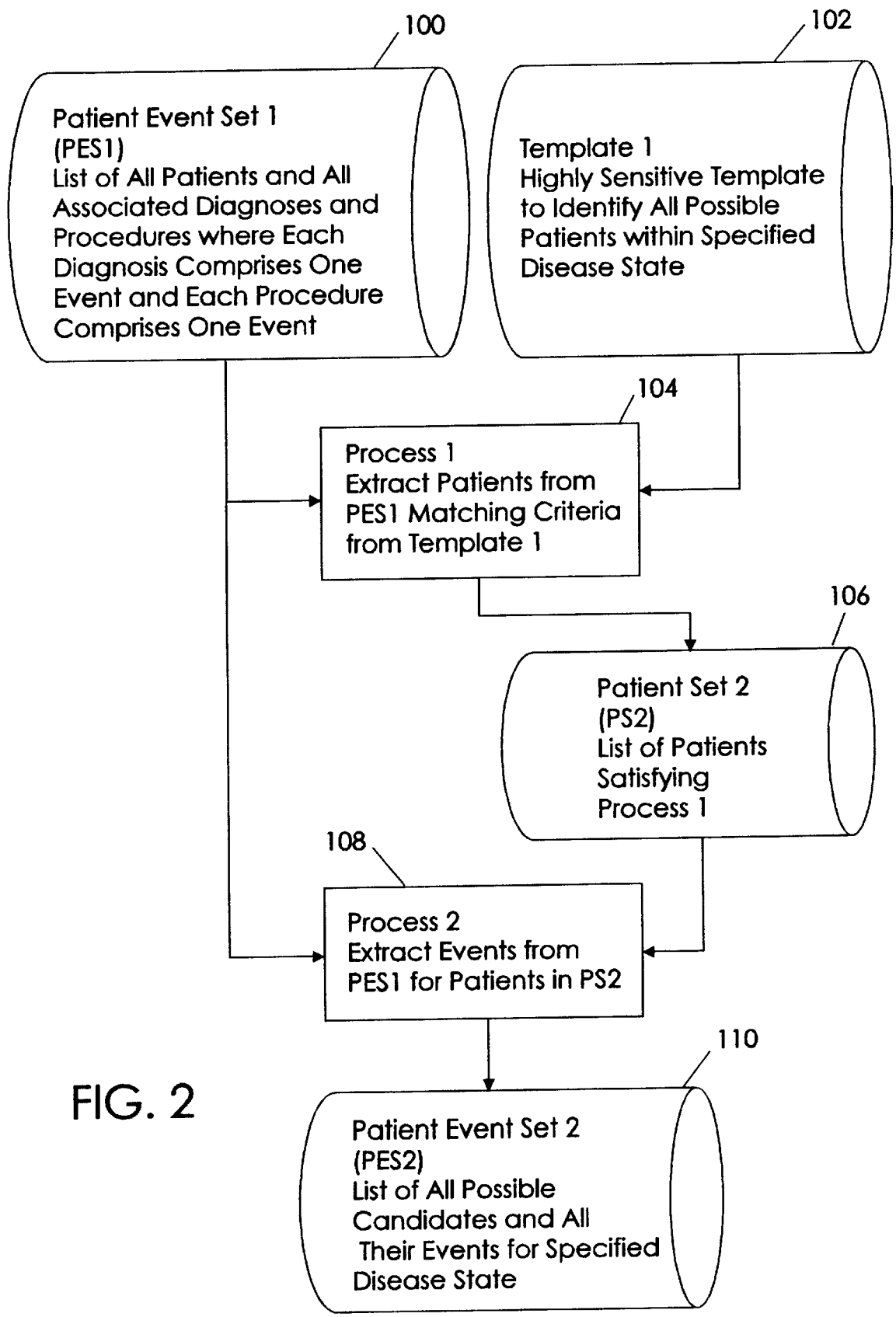
FIGS. 2–9 are flow charts schematically illustrating operations for identifying members of a population having a rare chronic disease, according to the present invention.

Referring now to FIG. 2, operations for identifying members of a population having a rare chronic disease, according to the present invention, will now be described. Patient Event Set 1 (PES1) (Block 100) is a population from which persons having a rare chronic disease are to be identified. PES1 (Block 100) contains a list of people and related medical "events" available for analysis. Created from each person's medical insurance claims history, an event is defined to include a medical procedure (i.e., visiting a medical practitioner), a diagnosis (i.e., an earache), and a drug (i.e., penicillin). For example, a patient that visits a doctor and is diagnosed with a cold and given penicillin has a minimum of three events associated therewith. Each event combined with a patient is defined as a "patient-event."

Template 1 (Block 102) contains a set of sensitive searches for the rare chronic disease under investigation. The rules for application include the boolean "or" operation. If any of the codes are found in the claims history, the patient will meet the initial filter. An exemplary Template 1 is illustrated below in Table 3.

Template 1 (Block 102) is applied to the patient-events in PES1 (Block 100) via Process 1 (Block 104) to extract from PES1 a list of all patients that could possibly have the specified rare chronic disease. It is expected that a large percentage of patients not having the rare chronic disease will be identified via Process 1 (Block 104). However, Process 1 (Block 104) facilitates reducing the number of patient-events contained within PES1 (Block 100) to a more manageable dataset. The application of Template 1 (Block 102) to PES1 (Block 100) produces Patient Set 2 (PS2) (Block 106). PS2 (Block 106) contains a list of names of patients identified by Process 1 (Block 104), but does not contain events associated therewith. Template 1 (Block 102) is a sensitive test that will identify a large number of patients from the original population having the rare chronic disease. Although it is sensitive, it is not specific in that patients not having the rare chronic disease will be identified as well. As would be understood by those having skill in the art, Process 1 (Block 104) may be performed by known database query methods.

Using Process 2 (Block 108) each event associated with a patient name listed in PS2 (Block 106) is located in PES1 (Block 100) and is matched with the respective patient name to produce Patient Event Set 2 (PES2) (Block 110). PES2 (Block 110) contains a list of all patients possibly having the rare chronic disease and includes all events related to each respective patient. It is to be understood that Process 2 (Block 108) may not be necessary and that Template 1 (Block 102) may be applied to PES1 (Block 100) to produce PES2 (Block 110). However, because PES1 (Block 100) often contains billions of bytes of information in hundreds of millions of records, computer processing time can be exceedingly long without the two process approach described above. The combination of Process 1 (Block 104) and Process 2 (Block 108) may reduce the impact of computer storage and speed limitations. As would be understood by those having skill in the art, Process 2 (Block 108) may be performed by known database query methods.

Similarly, Process 4 (Block 118) and Process 6 (Block 128), described below, may be performed in a similar manner.

Figure 3:
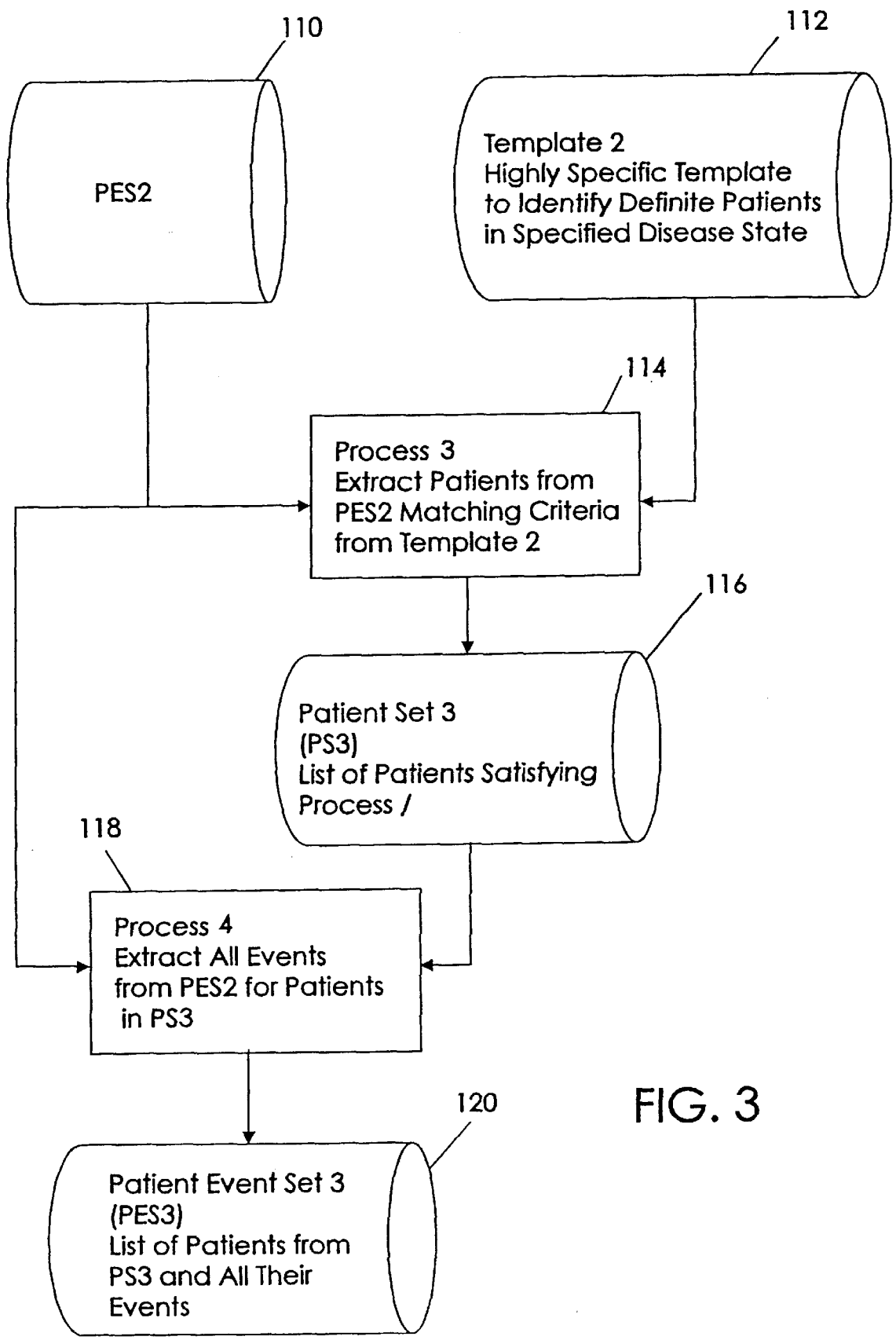

Referring now to FIG. 3, Template 2 (Block 112) is applied to PES2 (Block 110) in Process 3 (Block 114) to extract a list of patients from PES2 matching criteria set forth in Template 2. Template 2 (Block 112) is a highly specific template containing a set of specific searches for the rare chronic disease under investigation. The rules for application include boolean "or" operation. If any of the codes are formed in the claims history, the patient will meet the initial filter. The application of Template 2 (Block 112) to PES2 (Block 110) in Process 3 (Block 114) produces Patient Set 3 (PS3) (Block 116). PS3 (Block 116) contains a list of patients that have the rare chronic disease with a very high degree of certainty. Template 2 (Block 112) is a highly specific test that will identify a large number of patients having the rare chronic disease. Although it is possible that all patients having the rare chronic disease may not be listed within PS3 (Block 116), all patients listed within PS3 will likely have the rare chronic disease.

An exemplary Template 2 is illustrated below in Table 4.

TABLE 4

| Code | Rule |
| --- | --- |
| 277.0 | Three Diagnoses where none occurs in the same month |
| OR | |
| 277.0 | Three Diagnoses where none occurs in the same month |
| OR | |
| 277.01 | Three Diagnoses where none occurs in the same month |

Template 2 contains one or more rules relating to the rare chronic disease. For example, an exemplary rule for the rare chronic disease multiple sclerosis (MS) may include: taking the drug betaseron; diagnosed with MS five times; diagnosed with optic neuropathy; and confined to a wheelchair. A patient having events in his/her claim history complying with one or more of the rules in Template 2 will, in all likelihood, have the particular rare chronic disease in question. Thus, patients within PES2 (Block 110) satisfying one or more rules within Template 2 (Block 112) have, with high probability, the rare chronic disease.

Because PS3 (Block 116) contains only a list of patient names, the events associated with each patient are obtained from PES2 (Block 110) via Process 4 (Block 118). As described above with respect to Process 1 (Block 104) and Process 2 (Block 108), the combination of Process 3 (Block 114) and Process 4 (Block 118) reduces the impact of computer storage and speed limitations. However, it is to be understood that Process 4 (Block 118) may not be necessary and that Template 2 (Block 112) may be applied to PES2 (Block 110) to produce PES3 (Block 120). PES3 (Block 120) contains a list of patients, and their respective events, that, with high probability, have the rare chronic disease.

However, all possible patients from the original population, PES1 (Block 100), having the rare chronic disease are not included in PES3 (Block 3) because only the patients contained in PES3 passed the test indicated in Process 3 (Block 114).

Figure 4:
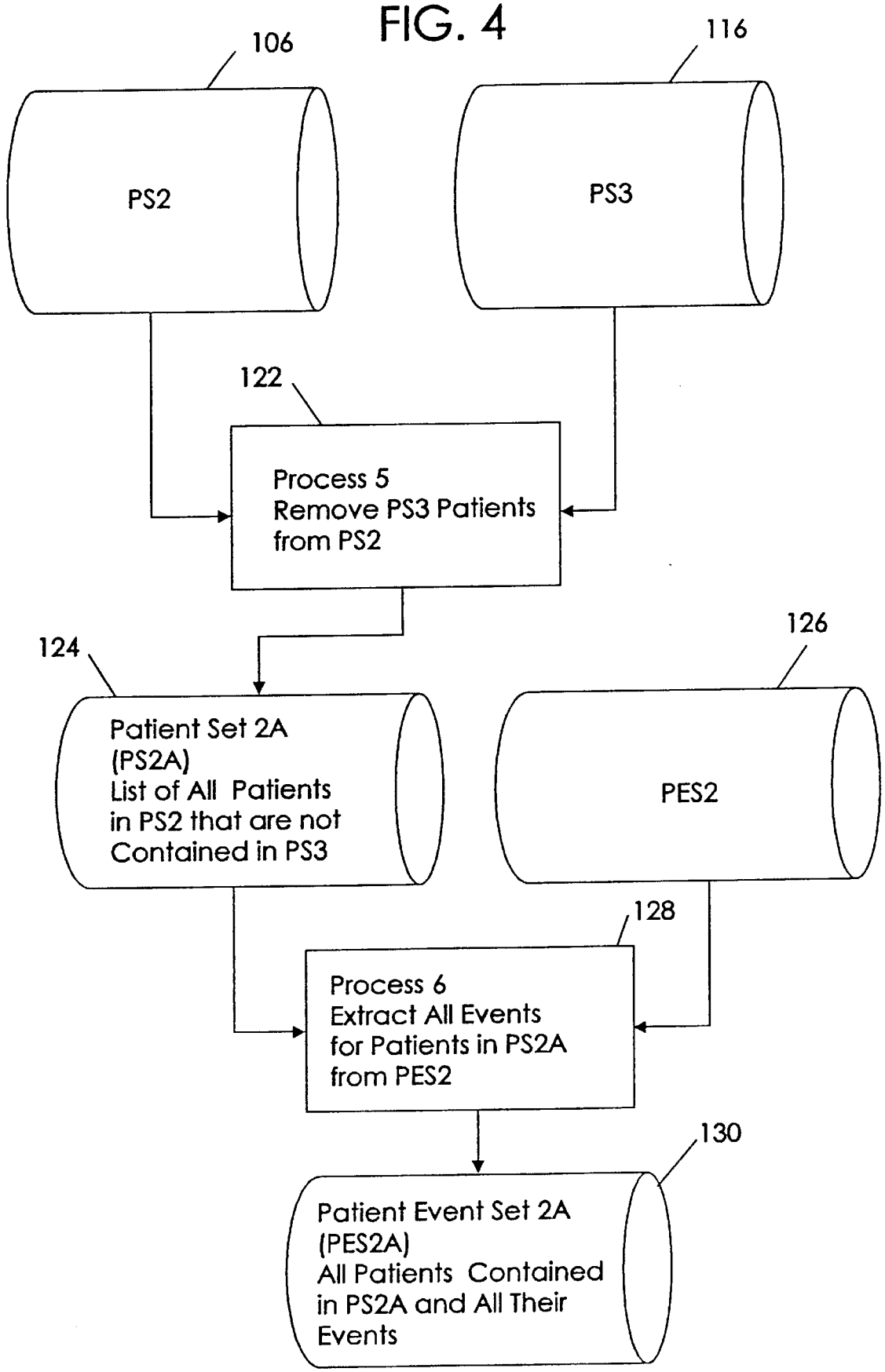

Referring now to FIG. 4, patients in PS3 (Block 116) are removed from PS2 (Block 106) via Process 5 (Block 122) to produce Patient Set 2A (PS2A) (Block 124). Process 5 (Block 122), removes the set of patients having the rare chronic disease from the set of patients possibly having the rare chronic disease. As a result, there are no duplicates between the two sets. Thus, any patient that is a member if PS2A (Block 124) is not a member of PS3 (Block 116). Stated another way, the combination of members of PS3 (Block 116) and members of PS2A (Block 124) produces the members of PS2 (Block 106). Thus, the members of PS2A are patients who possibly have the rare chronic disease, but who do not definitely have the rare chronic disease.

Because PS2A (Block 124) contains only names of the members therein, Process 6 (Block 128) is utilized to extract from PES2 (Block 126) all events associated with each respective member of PS2A. Process 6 (Block 128) performs its functions as described above with respect to Process 2 (Block 108) and Process 4 (Block 118). PES2A (Block 130) contains the patients within PS2A (Block 124) along with all events associated with each respective patient therewithin. It is noted that Process 6 (Block 128) performs the same function as Process 2 (Block 108) and Process 4 (Block 118).

Figure 5:
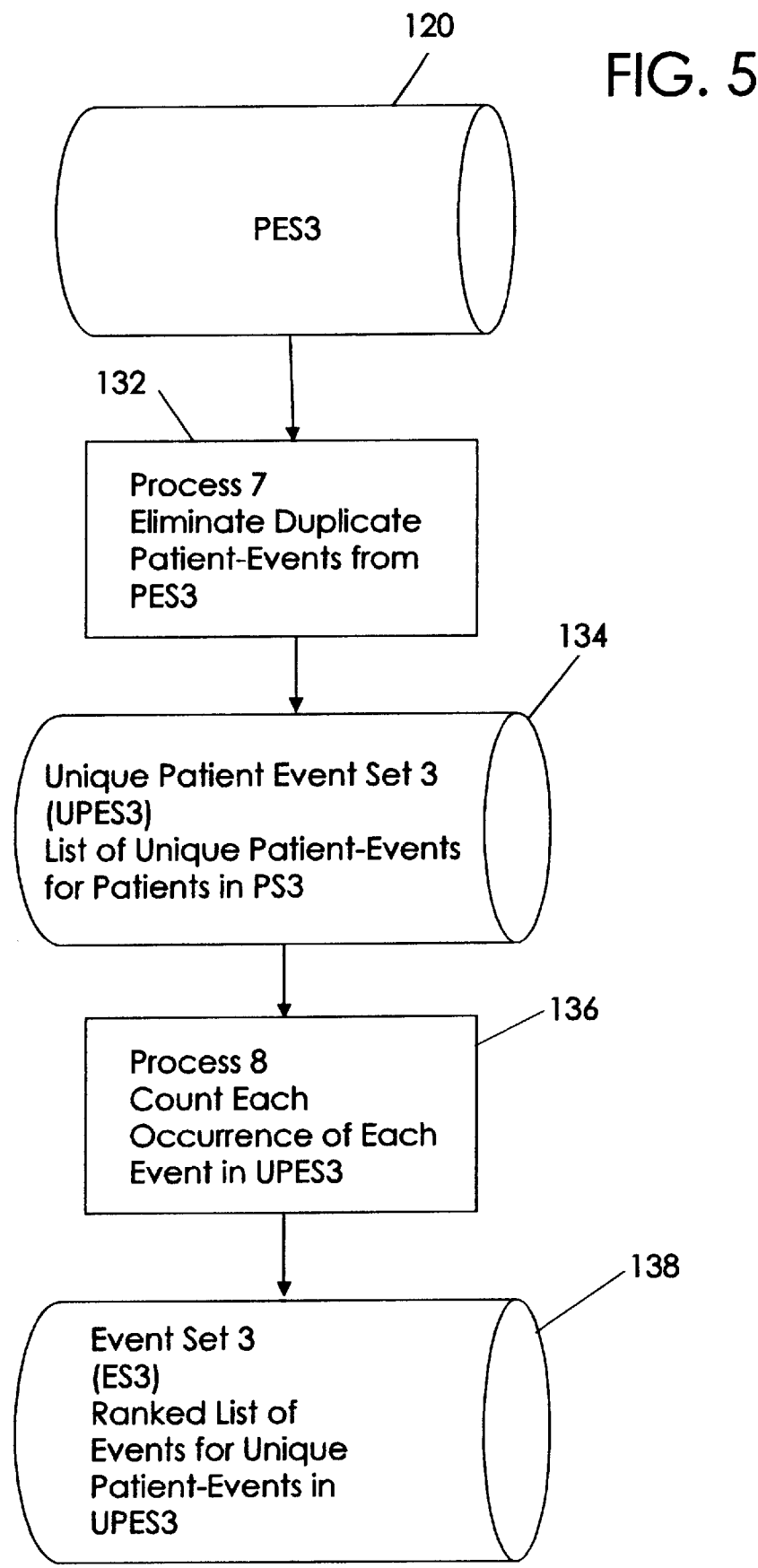

Referring now to FIG. 5, duplicate patient events are eliminated for each patient that is a member of PES3 (Block 120) via Process 7 (Block 132). For example, if a patient has been diagnosed as having a cold more than once in his or her claims history, only one event of being diagnosed as having a cold is kept and the rest of the identical events are eliminated. This produces Unique Patient Event Set 3 (UPES3) (Block 134) which is a list of patients that definitely have the rare chronic disease and every unique event that has happened to them. For example, if a patient has been put on the drug betaseron five times (i.e., five events), UPES3 (Block 134) contains only one unique event that the patient has been put on the drug betaseron. Other event-related information such as how many times and when the patient was placed on the drug betaseron is not included within UPES3 (Block 134).

The number of occurrences of each event in UPES3 (Block 134) is then counted and divided by the number of patients in PS3 via Process 8 (Block 136). For example, if twenty-five patients within UPES3 (Block 134) have taken the drug betaseron, the number of occurrences of this event is twenty-five. If the number of patients in PS3 is six-hundred (600), the frequency percentage is calculated by dividing twenty-five by six-hundred, which equals 4.17% (25/600=0.0417). The occurrences and frequency of occurrence of each event are then ranked to produce Event Set 3 (ES3) (Block 138). An exemplary ES3 is illustrated below in Table 5, wherein there are six-hundred (600) members of PS3.

TABLE 5

| Events | # of Occurrences | Frequency |
| --- | --- | --- |
| Took the Drug Betaseron | 116 | 19.3% |
| Diagnosis of MS | 104 | 17.3% |
| Admitted to Hospital | 82 | 13.7% |
| Diagnosis of Cold | 10 | 1.7% |
| Confined to a Wheelchair | 3 | 0.5% |

Patient names are not listed in ES3 (Block 138), only each unique event, the number of occurrences of each unique event, and the frequency of occurrence as determined via Process 8 (Block 136).

Figure 6:
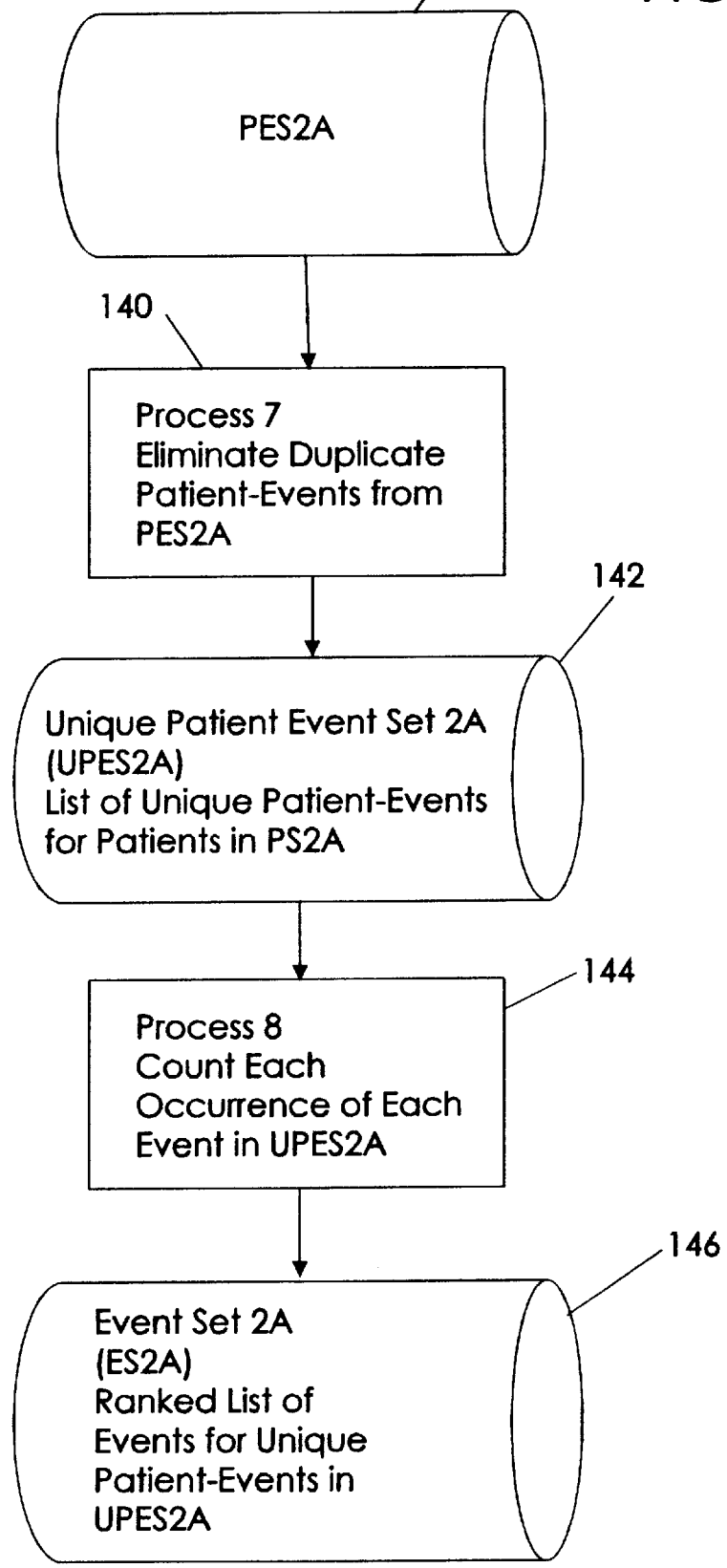

Referring now to FIG. 6, the above described process is performed with respect to PES2A. Duplicate patient events are eliminated for each patient that is a member of PES2A (Block 130) via Process 7 (Block 140). For example, if a patient has been diagnosed as having a cold more than once in his or her claims history, only one event of being diagnosed as having a cold is kept and the rest of the identical events are eliminated. This produces Unique Patient Event Set 2A (UPES2A) (Block 142) which is a list of patients that may have the rare chronic disease and every unique event that has happened to them. For example, if a patient has been put on the drug penicillin ten times (i.e., ten events), UPES2A (Block 142) contains only one unique event that the patient has been put on the drug penicillin. Other event-related information such as how many times and when the patient was placed on the drug penicillin is not included within UPES2A (Block 142).

The number of occurrences of each event in UPES2A (Block 142) is then counted and divided by the number of patients in PS2A via Process 8 (Block 144). For example, if twenty-five patients within UPES2A (Block 142) have taken the drug penicillin, the number of occurrences of this event is twenty-five. If the number of patients in PS2A is three-hundred-fifty (350), the frequency percentage is calculated by dividing twenty-five by three-hundred-fifty, which equals 7.14% (25/350=0.0714). The occurrences and frequency of occurrence of each event are then ranked to produce Event Set 2A (ES2A) (Block 146). An exemplary ES2A is illustrated below in Table 6, wherein there are three-hundred-fifty (350) members of PS2A.

TABLE 6

| Events | # of Occurrences | Frequency |
| --- | --- | --- |
| Took the Drug Penicillin | 79 | 22.6% |
| Diagnosis of MS | 59 | 16.8% |
| Admitted to Hospital | 55 | 15.7% |
| Diagnosis of Cold | 7 | 2.0% |
| Confined to a Wheelchair | 2 | 0.6% |

Patient names are not listed in ES2A (Block 146), only each unique event, the number of occurrences, and the frequency of occurrence of each unique event, as determined via Process 8 (Block 144), are contained therewithin. It is to be understood that operations for producing ES3 (Block 138) and ES2A (Block 146), as described above, can occur simultaneously or independently of each other.

Figure 7:
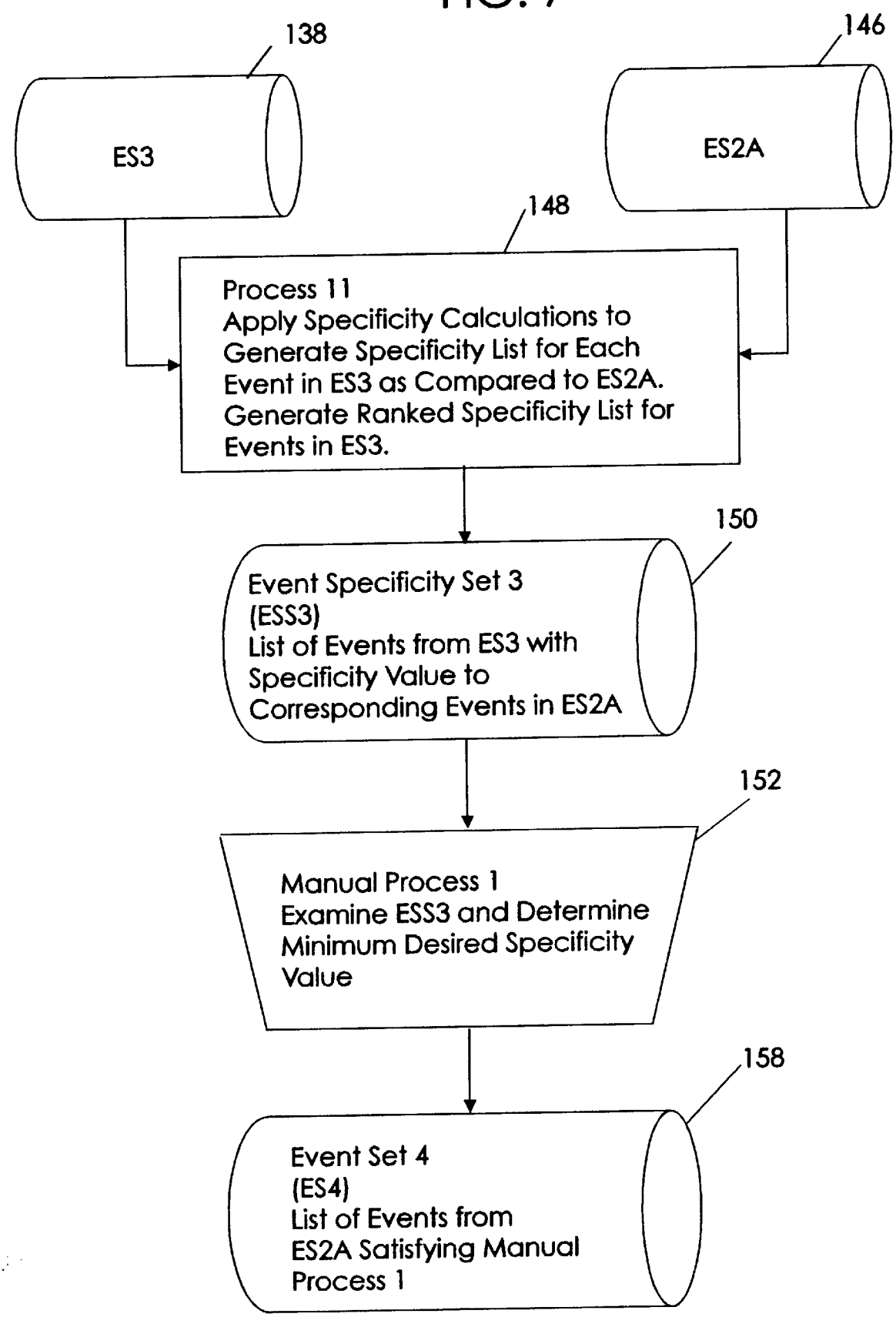

Referring now to FIG. 7, a comparison is made between the frequency of occurrence of an event per population in ES2A and the frequency of occurrence of an event per population in ES3. The goal is to generate a list of the events in ES3 with each event having a value indicating how specific the event is to the patients within PS3. This is referred to as the "specificity rating" for each event and is performed via Process 11 (Block 148).

In Process 11 (Block 148), the specificity rating for each event in ES3 and ES2A is calculated by dividing the smallest frequency of occurrence by the largest frequency of occurrence and then subtracting the results from one (1). For example, if the an event had a frequency of occurrence in ES3 of sixteen percent (16%) and a frequency of occurrence in ES2A of one percent (1%), the specificity rating is calculated as 1−(0.01/0.16)=0.9375. This indicates that the event is 93.75% specific to patients definitely having the rare chronic disease.

However, if the frequency of occurrence in ES3 is twenty-five percent (25%) and the frequency of occurrence in ES2A is thirty-one percent (31%), there is a negative specificity rating calculated as follows: 1−(0.25/0.31)=−0.1935. This negative specificity rating means that the event occurred more often to people probably, but not definitely, having the rare chronic disease. If the frequency of occurrence for an event is the same in both ES2A and ES3, the specificity rating is zero (0), which means that the event occurred equally as often in either set. If a negative specificity rating of −1.0 is obtained, this indicates that all patients probably having the rare chronic disease had the event happen to them, but none of the patients definitely having the rare chronic disease had the event happen to them.

After calculating the specificity rating for each event via Process 11 (Block 148), the events in ES3 are ranked by specificity rating and an Event Specificity Set 3 (ESS3) is generated (Block 150). The set ESS3 is then reviewed and a determination is made as to a minimum desired specificity value (Block 152). The selected minimum specificity value is then applied to set ES2A to extract all events having a specificity value greater than or equal to the minimum value. The resulting set of events is Event Set 4 (ES4) (Block 158). Thus, events included in ES4 are those having a specificity rating above the selected minimum value. Typically, the minimum specificity value is ninety-six percent to ninety-seven percent (96%–97%). However, other minimum specificity values may be utilized.

Figure 8:
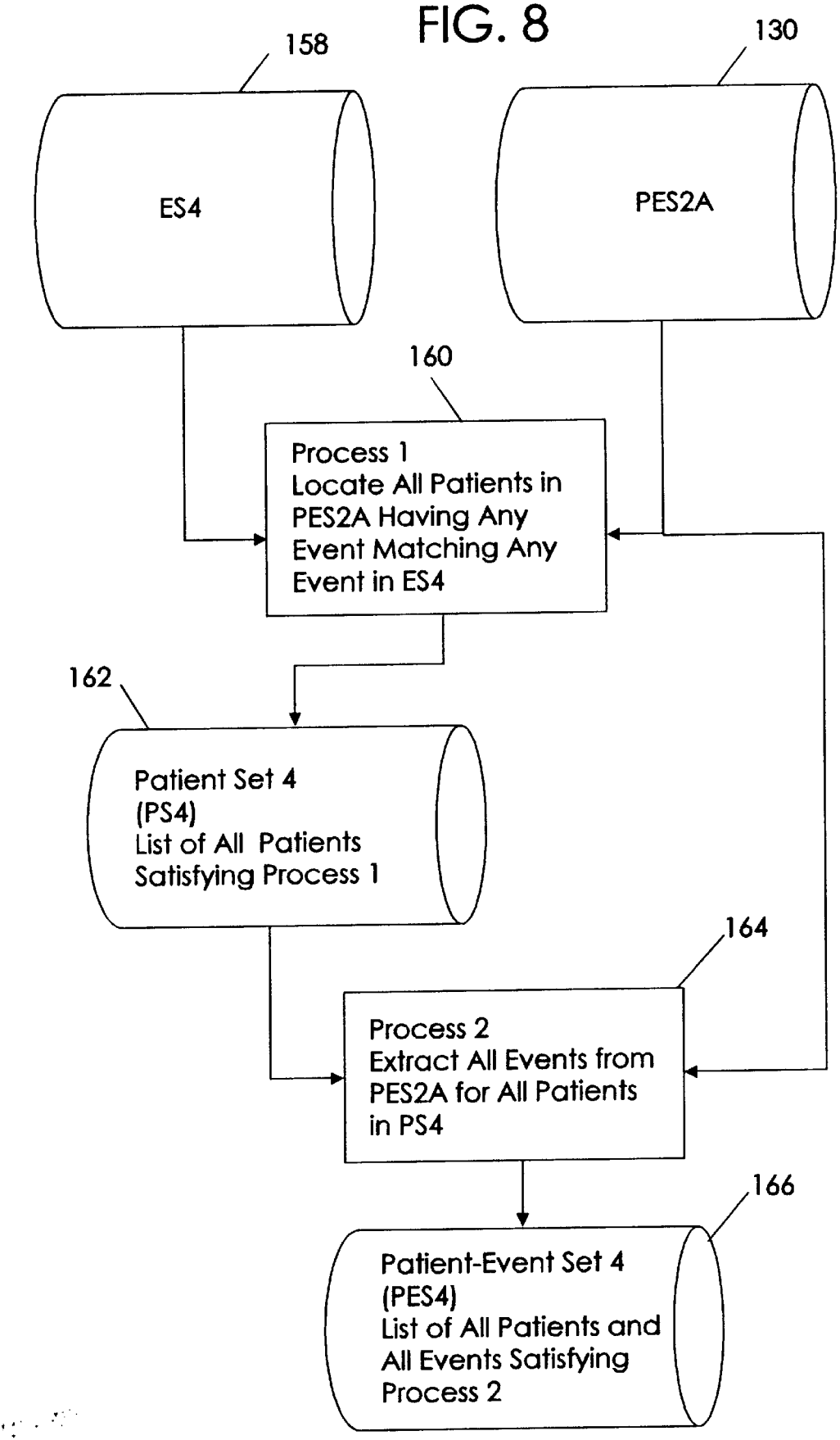

Referring now to FIG. 8, ES4 is utilized to identify all patients within set PES2A having an event associated therewith with a specificity value above the minimum value via Process 1 (Block 160). Process 1 (Block 160) performs its functions as described above with respect to Process 1 (Block 104) and Process 3 (Block 114). The resulting list of patients is Patient Set 4 (PS4) (Block 162). As described above, each event associated with a respective patient in PS4 is extracted from set PES2A via Process 2 (Block 164) to produce Patient Event Set 4 (PES4) (Block 166). Process 2 (Block 164) performs its functions as described above with respect to Process 2 (Block 108), Process 4 (Block 118), and Process 6 (Block 128).

Thus, a patient within set PES2A (the set of patients probably having the rare chronic disease) who has an event associated therewith with a high specificity value, does, in all likelihood, have the rare chronic disease. For example, if taking the drug betaseron is a highly specific event to patients known to have a rare chronic disease, then patients identified as probably having the rare chronic disease are going to have the disease if they have taken betaseron.

Figure 9:
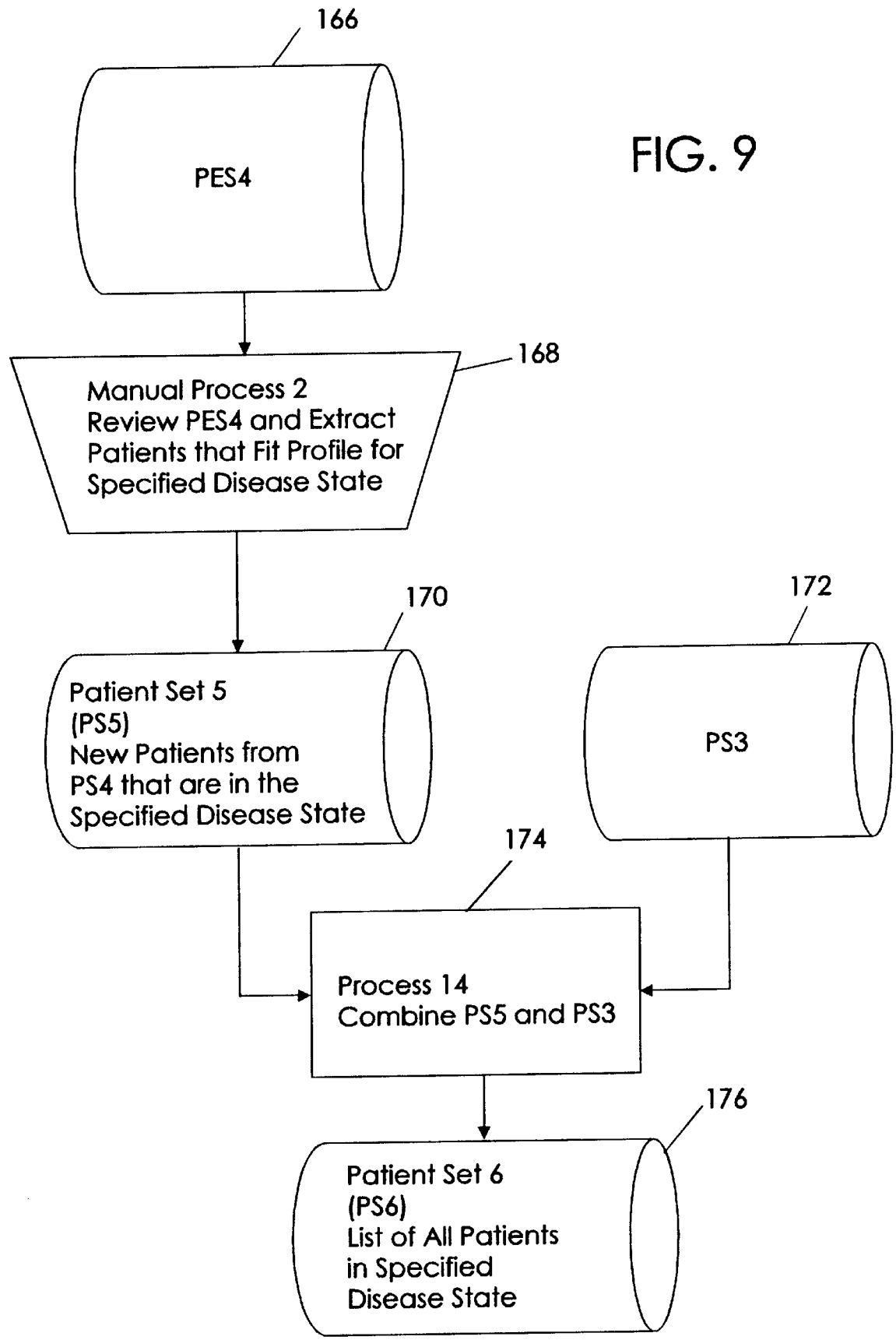

Referring now to FIG. 9, additional operations may include conducting a manual review of PES4 to identify patients that do or do not fit a profile for a specific rare chronic disease (Block 168). Patients that do satisfy the specific rare chronic disease are identified in Patient Set 5 (PS5) (Block 170). Sets PS5 and PS3 are then combined via Process 14 (Block 174) to produce Patient Set 6 (PS6) (Block 176). PS6 includes all patients having a specific rare chronic disease. Additionally, PS6 can be compared against PES1 via Process 2 to create Patient Event Set 6 (PES6), not shown. Renaming PS6 as PS3, operations between Blocks 122 and 176 may be repeated to yield additional patients having the specified rare chronic disease.

EXAMPLE

In a search for patients with Multiple Sclerosis (MS), an initial examination of all patients within the claims data (PS1), filtering for all patients with any occurrence of diagnoses including 340 (MS), 341, 341.8 or 341.9 (Other Demyelinating Diseases of the Central Nervous System), or 377.3 or 377.30 (Optic Neuritis) yields twenty to twenty five times the expected number of patients because patients that do not have MS are included. To pursue identification of the patients, then, this list (PS2) is subjected to a highly specific search in which only patients with multiple diagnoses over time or diagnoses combined with specific procedures or that have specific drugs in their claims history are located. That set (PS3) may contain only one third to one half the expected number of patients, but contains only MS patients.

We expect MS patients to have some items in common. We therefore list all events that are contained in the claims history of the known list (PS3) and count the number of patients that have each event and determine the percentage of patients having each event. We then look at the general population and count the number of patients that have each of the events listed and determine the percentage of patients having each event.

Comparing the percentage of patients having an event in their claims history with the percentage of patients in the known MS population having the same event, we determine whether an event is highly specific to the MS population. We then continue by ranking that comparison which is then identified as the correlated event specificity subset. When we finish the ranking, we can see, in tabular form, those events that are most important to identifying the MS patients in that particular database.

Next, we search the general population for events or combinations of events which are highly specific (perhaps 97% specific, but the percentage may vary with each database and is subject to human evaluation). This gives a list of patients that are quite likely to have MS. The entire event set for each of those patients is then printed and subjected to a review by an expert medical team and a finalized review list (PS5) is tabulated. The combined lists of PS2 and PS5 comprises the list of MS patients in the database The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clause are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. A method of identifying members of a population having a rare chronic disease, wherein each member of said population has at least one medical event associated therewith, said method comprising the following steps which are performed on a data processing system:

(a) identifying a first set of medical events associated with said rare chronic disease;
   (b) creating a first population subset from said population, each member of said first subset having associated therewith at least one medical event from said identified first set of medical events;
   (c) identifying a second set of medical events associated with said rare chronic disease;
   (d) creating a second population subset from said first population subset, each member of said second population subset having associated therewith at least one medical event from said identified second set of medical events;
   (e) creating a third population subset, said third population subset comprising members of said first population subset who are not members of said second population subset;
   (f) determining a frequency of occurrence for each medical event associated with members of said second population subset;
   (g) determining a frequency of occurrence for each medical event associated with members of said third population subset;
   (h) assigning a specificity rating to each medical event associated with members of said second population subset, each specificity rating identifying how often a respective medical event occurred within said second population subset relative to said third population subset;
   (i) identifying a third set of medical events associated with members of said second population subset, each of said identified medical events having a specificity rating above a selected threshold;
   (j) creating a fourth population subset from said third population subset, each member of said fourth population subset having associated therewith at least one medical event from said third set of medical events; and
   (k) combining said second and fourth population subsets, thereby identifying members of said population having a rare chronic disease.

2. A method according to claim 1 wherein each one of said medical events comprises a medical symptom, medical diagnosis, medical treatment, or combination thereof, of a respective population member.

3. A method according to claim 1 wherein said step (j) further comprises selectively removing from said fourth population members having medical events and conditions associated therewith that are preemptive of said rare chronic disease.

4. A method according to claim 1 further comprising adjusting said selected specificity rating threshold in step (i) and performing said steps (i) through (k) to identify members of said population having a rare chronic disease.

5. A data processing system for identifying members of a population having a rare chronic disease, wherein each member of said population has at least one medical event associated therewith, said data processing system comprising:

(a) means for identifying a first set of medical events associated with said rare chronic disease;
   (b) means for creating a first population subset from said population, each member of said first subset having associated therewith at least one medical event from said identified first set of medical events;
   (c) means for identifying a second set of medical events associated with said rare chronic disease;
   (d) means for creating a second population subset from said first population subset, each member of said second population subset having associated therewith at least one medical event from said identified second set of medical events;
   (e) means for creating a third population subset, said third population subset comprising members of said first population subset who are not members of said second population subset;
   (f) means for determining a frequency of occurrence for each medical event associated with members of said second population subset;
   (g) means for determining a frequency of occurrence for each medical event associated with members of said third population subset;
   (h) means for assigning a specificity rating to each medical event associated with members of said second population subset, each specificity rating identifying how often a respective medical event occurred within said second population subset relative to said third population subset;

(i) means for identifying a third set of medical events associated with members of said second population subset, each of said identified medical events having a specificity rating above a selected threshold;

(j) means for creating a fourth population subset from said third population subset, each member of said fourth population subset having associated therewith at least one medical event from said third set of medical events; and (k) means for combining said second and fourth population subsets, thereby identifying members of said population having a rare chronic disease.

6. A data processing system according to claim 5 wherein each one of said medical events comprises a medical symptom, medical diagnosis, medical treatment, or combination thereof, of a respective population member.

7. A data processing system according to claim 5 wherein said means for creating a fourth population subset from said third population subset comprises means for selectively removing from said fourth population members having medical events and conditions associated therewith that are preemptive of said rare chronic disease.

8. A data processing system according to claim 5 wherein said means for identifying a third set of medical events associated with members of said second population subset comprises means for adjusting said selected specificity rating threshold.

9. A computer program product for use with a data processing system for identifying members of a population having a rare chronic disease, wherein each member of said population has at least one medical event associated therewith, said computer program product comprising:

(a) a computer usable medium having computer readable program code means embodied in said medium for identifying a first set of medical events associated with said rare chronic disease;

(b) the computer usable medium having computer program code means embodied in said medium for creating a first population subset from said population, each member of said first subset having associated therewith at least one medical event from said identified first set of medical events;

(c) the computer usable medium having computer program code means embodied in said medium for identifying a second set of medical events associated with said rare chronic disease;

(d) the computer usable medium having computer program code means embodied in said medium for creating a second population subset from said first population subset, each member of said second population subset having associated therewith at least one medical event from said identified second set of medical events;

(e) the computer usable medium having computer program code means embodied in said medium for creating a third population subset, said third population subset comprising members of said first population subset who are not members of said second population subset;

(f) the computer usable medium having computer program code means embodied in said medium for determining a frequency of occurrence for each medical event associated with members of said second population subset;

(g) the computer usable medium having computer program code means embodied in said medium for determining a frequency of occurrence for each medical event associated with members of said third population subset;

(h) the computer usable medium having computer program code means embodied in said medium for assigning a specificity rating to each medical event associated with members of said second population subset, each specificity rating identifying how often a respective medical event occurred within said second population subset relative to said third population subset;

(i) the computer usable medium having computer program code means embodied in said medium for identifying a third set of medical events associated with members of said second population subset, each of said identified medical events having a specificity rating above a selected threshold;

(j) the computer usable medium having computer program code means embodied in said medium for creating a fourth population subset from said third population subset, each member of said fourth population subset having associated therewith at least one medical event from said third set of medical events; and (k) the computer usable medium having computer program code means embodied in said medium for combining said second and fourth population subsets, thereby identifying members of said population having a rare chronic disease.

10. A computer program product according to claim 9 wherein each one of said medical events comprises a medical symptom, medical diagnosis, medical treatment, or combination thereof, of a respective population member.

11. A computer program product according to claim 9 wherein said computer readable program code means for creating a fourth population subset from said third population subset comprises computer readable program code means, embodied in said media, for selectively removing from said fourth population members having medical events and conditions associated therewith that are preemptive of said rare chronic disease.

12. A computer program product according to claim 9 wherein said computer readable program code means for identifying a third set of medical events associated with members of said second population subset comprises computer readable program code means, embodied in said media, for adjusting said selected specificity rating threshold.

13. A method of identifying members of a population having a rare chronic disease, wherein each member of said population has at least one medical event associated therewith, said method comprising the following steps which are performed on a data processing system:

(a) identifying a first set of medical events associated with said rare chronic disease;

(b) creating a first population subset from said population, each member of said first subset having associated therewith at least one medical event from said identified first set of medical events;

(c) creating a second population subset, said second population subset comprising members of said population who are not members of said first population subset;

(d) determining a frequency of occurrence for each medical event associated with members of said first population subset;

(e) determining a frequency of occurrence for each medical event associated with members of said second population subset;

(f) assigning a specificity rating to each medical event associated with members of said first population subset, each specificity rating identifying how often a respective medical event occurred within said first population subset relative to said second population subset;

(g) identifying a second set of medical events associated with members of said first population subset, each of said identified medical events having a specificity rating above a selected threshold;

(h) creating a third population subset from said second population subset, each member of said third population subset having associated therewith at least one medical event from said second set of medical events; and (i) combining said first and third population subsets, thereby identifying members of said population having a rare chronic disease.

14. A method according to claim 13 wherein each one of said medical events comprises a medical symptom, medical diagnosis, medical treatment, or combination thereof, of a respective population member.

15. A method according to claim 13 wherein said step (h) further comprises selectively removing from said third population members having medical events and conditions associated therewith that are preemptive of said rare chronic disease.

16. A method according to claim 13 further comprising adjusting said selected specificity rating threshold in step (g) and performing said steps (g) through (i) to identify members of said population having a rare chronic disease.

17. A data processing system for identifying members of a population having a rare chronic disease, wherein each member of said population has at least one medical event associated therewith, said data processing system comprising:

(a) means for identifying a first set of medical events associated with said rare chronic disease;

(b) means for creating a first population subset from said population, each member of said first subset having associated therewith at least one medical event from said identified first set of medical events;

(c) means for creating a second population subset, said second population subset comprising members of said population who are not members of said first population subset;

(d) means for determining a frequency of occurrence for each medical event associated with members of said first population subset;

(e) means for determining a frequency of occurrence for each medical event associated with members of said second population subset;

(f) means for assigning a specificity rating to each medical event associated with members of said first population subset, each specificity rating identifying how often a respective medical event occurred within said first population subset relative to said second population subset;

(g) means for identifying a second set of medical events associated with members of said first population subset, each of said identified medical events having a specificity rating above a selected threshold;

(h) means for creating a third population subset from said second population subset, each member of said third population subset having associated therewith at least one medical event from said second set of medical events; and (i) means for combining said first and third population subsets, thereby identifying members of said population having a rare chronic disease.

18. A data processing system according to claim 17 wherein each one of said medical events comprises a medical symptom, medical diagnosis, medical treatment, or combination thereof, of a respective population member.

19. A data processing system according to claim 17 wherein said means for creating a third population subset from said second population subset comprises means for selectively removing from said third population members having medical events and conditions associated therewith that are preemptive of said rare chronic disease.

20. A data processing system according to claim 17 wherein said means for identifying a second set of medical events associated with members of said first population subset comprises means for adjusting said selected specificity rating threshold.

21. A computer program product for use with a data processing system for identifying members of a population having a rare chronic disease, wherein each member of said population has at least one medical event associated therewith, said computer program product comprising:

(a) a computer usable medium having computer readable program code means embodied in said medium for identifying a first set of medical events associated with said rare chronic disease;

(b) the computer usable medium having computer program code means embodied in said medium for creating a first population subset from said population, each member of said first subset having associated therewith at least one medical event from said identified first set of medical events;

(c) the computer usable medium having computer program code means embodied in said medium for creating a second population subset, said second population subset comprising members of said population who are not members of said first population subset;

(d) the computer usable medium having computer program code means embodied in said medium for means for determining a frequency of occurrence for each medical event associated with members of said first population subset;

(e) the computer usable medium having computer program code means embodied in said medium for means for determining a frequency of occurrence for each medical event associated with members of said second population subset;

(f) the computer usable medium having computer program code means embodied in said medium for assigning a specificity rating to each medical event associated with members of said first population subset, each specificity rating identifying how often a respective medical event occurred within said first population subset relative to said second population subset;

(g) the computer usable medium having computer program code means embodied in said medium for identifying a second set of medical events associated with members of said first population subset, each of said identified medical events having a specificity rating above a selected threshold;

(h) the computer usable medium having computer program code means embodied in said medium for creating a third population subset from said second population subset, each member of said third population subset having associated therewith at least one medical event from said second set of medical events; and (i) the computer usable medium having computer program code means embodied in said medium for combining said first and third population subsets, thereby identifying members of said population having a rare chronic disease.

22. A computer program product according to claim 21 wherein each one of said medical events comprises a medical symptom, medical diagnosis, medical treatment, or combination thereof, of a respective population member.

23. A computer program product according to claim 21 wherein said computer readable program code means for creating a third population subset from said second population subset comprises computer readable program code means, embodied in said media, for selectively removing from said third population members having medical events and conditions associated therewith that are preemptive of said rare chronic disease.

24. A computer program product according to claim 21 wherein said computer readable program code means for identifying a second set of medical events associated with members of said first population subset comprises computer readable program code means, embodied in said media, for adjusting said selected specificity rating threshold.

25. A method of identifying members of a population having a rare chronic disease, wherein each member of said population has at least one medical event associated therewith, said method comprising the steps of:

creating a first population subset from said population, each member of the second population subset having associated therewith at least one medical event from a first set of medical events;

creating a second population subset from said population, each member of the second population subset having associated therewith at least one medical event from a second set of medical events;

assigning a specificity rating to each medical event associated with members of said first and second population subsets, wherein each specificity rating identifies how often a respective medical event occurred within one of the first and second population subsets relative to the other one of the first and second population subsets; and processing said specificity ratings in order to identify members of said population having a rare chronic disease.

26. A method according to claim 25 wherein each one of said medical events comprises a medical symptom, medical diagnosis, medical treatment, or combination thereof, of a respective population member.

27. A data processing system for identifying members of a population having a rare chronic disease, wherein each member of said population has at least one medical event associated therewith, said data processing system comprising:

a database including patient and medical events;

means for creating within said database a first population subset from said population, each member of the first population subset having associated therewith at least one medical event from a first set of medical events;

means for creating within said database a second population subset from said population, each member of the second population subset having associated therewith at least one medical event from a second set of medical events;

means for assigning a specificity rating to each medical event within said database associated with members of said first and second population subsets, wherein each specificity rating identifies how often a respective medical event occurred within one of the first and second population subsets relative to the other one of the first and second population subsets; and means for processing said specificity ratings in order to identify members of said population having a rare chronic disease.

28. A data processing system according to claim 27 wherein each one of said medical events comprises a medical symptom, medical diagnosis, medical treatment, or combination thereof, of a respective population member.

* * * * *

UNITED STATES PATENT AND TRADEMARK OFFICE
CERTIFICATE OF CORRECTION

PATENT NO. : 5,956,689
DATED : September 21, 1999
INVENTOR(S) : Everhart, III

It is certified that error appears in the above-identified patent and that said Letters Patent is hereby corrected as shown below:

In the Claims:

Column 17, line 33, delete "second" and insert - - first - - in its place.

Signed and Sealed this

Eighth Day of August, 2000

Attest:

Q. TODD DICKINSON

*Attesting Officer*  *Director of Patents and Trademarks*